United States Patent [19]

Deno

[11] Patent Number: 5,507,785
[45] Date of Patent: Apr. 16, 1996

[54] RATE RESPONSIVE CARDIAC PACEMAKER WITH BIPHASIC IMPEDANCE SENSING AND METHOD

[75] Inventor: Don C. Deno, Missouri City, Tex.

[73] Assignee: Intermedics, Inc., Angleton, Tex.

[21] Appl. No.: 360,392

[22] Filed: Dec. 21, 1994

[51] Int. Cl.$^6$ ................................................. A61N 1/365
[52] U.S. Cl. ................................................. 607/24
[58] Field of Search ............................... 607/20, 24, 72; 128/734

[56] References Cited

U.S. PATENT DOCUMENTS

| | | |
|---|---|---|
| 4,686,987 | 8/1987 | Salo et al. . |
| 4,702,253 | 10/1987 | Nappholz et al. ........................ 607/20 |
| 4,901,725 | 2/1990 | Nappholz et al. . |
| 5,137,019 | 8/1992 | Pederson et al. ........................ 607/20 |
| 5,154,171 | 10/1992 | Chirife . |
| 5,197,467 | 3/1993 | Steinhaus et al. . |
| 5,201,808 | 4/1993 | Steinhaus et al. . |

OTHER PUBLICATIONS

Horowitz and Winfield, Ed. *The Art of Electronics*, 2nd. Ed., Cambridge Univ. Press, 1989, pp. 88–90.

*Primary Examiner*—William E. Kamm
*Assistant Examiner*—Scott M. Getzow
*Attorney, Agent, or Firm*—John R. Merkling

[57] ABSTRACT

An implantable, rate responsive pacemaker, sensitive to impedance changes in the heart as an indicator of cardiac stroke volume or minute volume, wherein common interfering signals such as the intracardiac electrogram, myoelectric signals, pacing artifacts and other pacing after potentials are reduced or eliminated from the measurement of the impedance by the use of a biphasic test signal. The cardiac pacemaker has a signal injector which produces biphasic test pulses of similar duration and magnitude and of constant current, though of opposite polarity. The pacemaker also has a detector which senses voltage resulting from the applied biphasic current pulses in each phase. Since the injector and detector are separate circuits, they can be used with a variety of electrode configurations.

20 Claims, 2 Drawing Sheets

5,507,785

RATE RESPONSIVE CARDIAC PACEMAKER WITH BIPHASIC IMPEDANCE SENSING AND METHOD

FIELD OF MY INVENTION

My invention relates to rate responsive cardiac pacemakers, and more particularly to cardiac pacemakers which automatically adjust their pacing parameters, for example the pacing rate, in response to measured impedance, and most particularly in response to measured impedance changes in the heart.

BACKGROUND OF MY INVENTION

Implanted cardiac pacemakers are employed to assist patients suffering from severe bradycardia or chronotropic incompetence. Originally, such pacemakers restored a normal, at rest, heart rate by providing a fixed rate or narrow range of externally programmable rates. However, these pacemakers failed to meet patients' metabolic demands during exercise. Consequently, so-called "rate adaptive" or "rate responsive" pacemakers were developed. These pacemakers sense some parameter correlated to physiologic need and adjust the pacing rate of the pacemaker.

Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Among these parameters are the stroke volume of the heart and the minute volume of respiration, both parameters being inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. For certain patients with pacemakers whose heart rate is controlled by the pacemaker, increased cardiac output during exertion is provided by the heart attempting to increase its stroke volume. The stroke volume cannot increase, however, by a factor more than about two or two and a half times. Increasing the pacing rate is therefore still desired. It has been proposed to utilize the body's tendency to attempt to increase stroke volume to adjust the pacing rate of an implanted pacemaker, thereby providing an appropriate physiologic pacing rate.

For example, in Salo et al., U.S. Pat. No. 4,686,987 a stroke volume responsive, rate adjusting pacemaker is described. An AC signal is inserted through an implanted lead. The changing volume of the heart alters the impedance between the lead electrode and another electrode or the can of the pacemaker, and the changing impedance modulates the detected AC signal. By isolating the resulting amplitude envelope, an indication of the changing impedance can be obtained. This fluctuation is deemed to be a function, at least in part, of the action of the heart.

Chirife, U.S. Pat. No. 5,154,171, proposed that metabolic demands should be related to the ejection fraction, as a more accurate measure of true physiologic need. The ejection fraction is the stroke volume divided by the end diastolic volume. The stroke volume is taken to be the end diastolic volume minus the end systolic volume. The observed impedance of the heart is deemed to be a function of volume of the heart and therefore to be an indication of the desired measurements when taken at an appropriate time.

In practice, intracardiac impedance measurements reflect electrical conductivity in other parts of the body and are not solely related to the beating of the heart. Other motions and factors also change the impedance characteristics. One example is change due to respiration. It has been proposed that the minute volume of respiration could be detected by an appropriate impedance measurement. See, for example, U.S. Pat. No. 4,901,725 entitled "Minute Volume Rate Responsive Pacemaker" to Nappholz et al.

U.S. Pat. No. 5,201,808 to Steinhaus et al., describes several attempts to detect the minute volume due to respiration in an accurate manner. Steinhaus et al. also proposes a relatively high frequency waveform as the appropriate means for measuring the spatial impedance as a function of the patient's pleural pressure. Steinhaus et al. notes that different frequencies for the testing pulse are adapted to detecting different phenomenon. That is, one range of frequency may be more appropriate for detecting changes due to heart beats, another would be more appropriate for detecting minute volume.

U.S. Pat. No. 5,197,467 to Steinhaus, et al. describes charging a capacitor (see particularly FIG. 2) and discharging the capacitor through the heart or a portion of the body for a selected brief interval. The voltage remaining on the capacitor after the period of discharge can be detected through a buffer, converted to digital information, and used to estimate the impedance of that portion of the patient's body between the cathode and anode electrodes.

However, a problem raised by the use of impedance as an indirect measure of physiologic need is the indeterminate current path. The impedance of the body is generally measured between at least two points within the body, perhaps an electrode in the heart and a second electrode or the can of an implanted device. The path between these to points, however, is inherently indeterminate. Moreover, the measurement may be affected by motion of the electrode tip, by conditions surrounding the tip or by electrical capacitances adjacent electrodes (as described in Steinhaus et al. '808), or other factors. Myopotentials, pacing artifacts, pacing afterpotentials, and general electrical noise can all mask the desired measurement. It is desirable, therefore, to eliminate or minimize the effect of background interference or apparent baseline impedance so that changes in impedance due to the relatively fast beating heart or to respiration may be amplified and more easily detected.

One approach to solving the problem of electrical noise has been proposed by Prutchi in co-pending, commonly assigned application Ser. No. 08/342,436, filed Nov. 18, 1994, incorporated herein by reference. Prutchi discloses a cardiac pacemaker which senses varying impedance of the heart by discharging an active capacitor through an electrode implanted within the heart to a second electrode or to the case or can of the pacemaker. The active capacitor is discharged for a selected short period of time after which the voltage remaining on the capacitor is buffered for further processing. Prior to discharge of this active capacitor, however, the cardiac pacemaker samples the electrical condition of the heart or the body of the patient between the two electrodes by charging a passive capacitor. The voltage on this passive capacitor is also buffered and held in a sample and hold circuit until the active capacitor has been discharged. The voltage on the passive capacitor is subtracted from the residual voltage on the active capacitor and the resulting voltage is held in a sample and hold circuit. The voltage held in the sample and hold circuit is communicated to a microprocessor for adjustment of the rate of the pacemaker.

SUMMARY OF MY INVENTION

I have invented an implantable, rate responsive pacemaker, sensitive to impedance changes in the heart as an indicator of cardiac stroke volume or minute volume, wherein common interfering signals such as the intracardiac electrogram, myoelectric signals, pacing artifacts and other pacing after potentials are reduced or eliminated from the measurement of the impedance by the use of a biphasic test signal and measurement process. The cardiac pacemaker of my invention has a signal injector which produces biphasic test pulses of very brief duration, for example, between two and fifty microseconds. The pulses are preferably of similar duration and magnitude, though of opposite polarity. They are delivered by the signal injector across a selected set of electrodes. The pulses are preferably of substantially constant current.

The pacemaker of my invention also has a detector which senses voltage resulting from the applied biphasic current pulses in each phase. Preferably, the two voltages are combined to eliminate many sources of sensor noise or other error, while simultaneously adding the magnitude of the desired, impedance-related voltages providing a more accurate measurement.

Use of very brief pulses in a biphasic fashion in close proximity helps to prevent false sensing by digital or other ECG monitors or by transtelephonic monitors because the two pulses tend to neutralize each other's effect. Moreover, use of a constant current biphasic technique is less sensitive to sensor noise as contrasted to measurements related to discharge of a capacitor. As an example, a one percent error in measurement of this sensed voltage is reflected in a corresponding one per cent error in estimated impedance. However, because of the shape of the discharge curve of the capacitor, a one percent error in measurement of the voltage sensed on a discharging capacitor corresponds to a 2.7 per cent or greater error in estimated impedance.

Another advantage of my invention is that the balanced biphasic current pulses assure that no net charge is transferred across the electrodes. This reduces electrode deposition and corrosion for greater biocompatability.

Since the injector and detector of my invention are separate circuits, they can be used with a variety of electrode configurations. This permits configurations to be established which reduce undesirable effects of contact geometry and extracardiac conduction. Both the injector and the detector have at least two electrodes associated with each. The injector and detector may be connected to share common electrodes, for a minimum of two electrodes; they may share one electrode, resulting in a configuration of three electrodes; or they use separate electrodes resulting in a configuration using four electrodes. If desired, the anode or cathode of either the detector or the injector may be subdivided to a plurality of locations.

It is the principal object of my invention, therefore, to provide a rate-responsive pacemaker which can more accurately detect impedance changes in the heart.

A further object of my invention is to provide an impedance sensitive pacemaker which can reject background and interference signals such as the intracardiac electrogram, myoelectric signals, pacing potential artifacts, and pacing after-potentials, for example.

Another object of my invention is to provide a rate responsive pacemaker which can amplify the effects of cardiac-related or metabolic demand related impedance changes.

Another important object of my invention is to provide a rate responsive pacemaker which is more selectively responsive to cardiac stoke volume changes, end systolic or end diastolic volumes as indicated by changes in cardiac impedance.

These and other objects and features of my invention will be apparent to the skilled artisan from the following detailed description taken with reference to the accompanying drawings.

DETAILED DESCRIPTION OF MY PREFERRED EMBODIMENT

I will now describe the preferred embodiment of my invention with reference to the accompanying figures. Like numerals will be used to designate like parts throughout.

Figure 1:
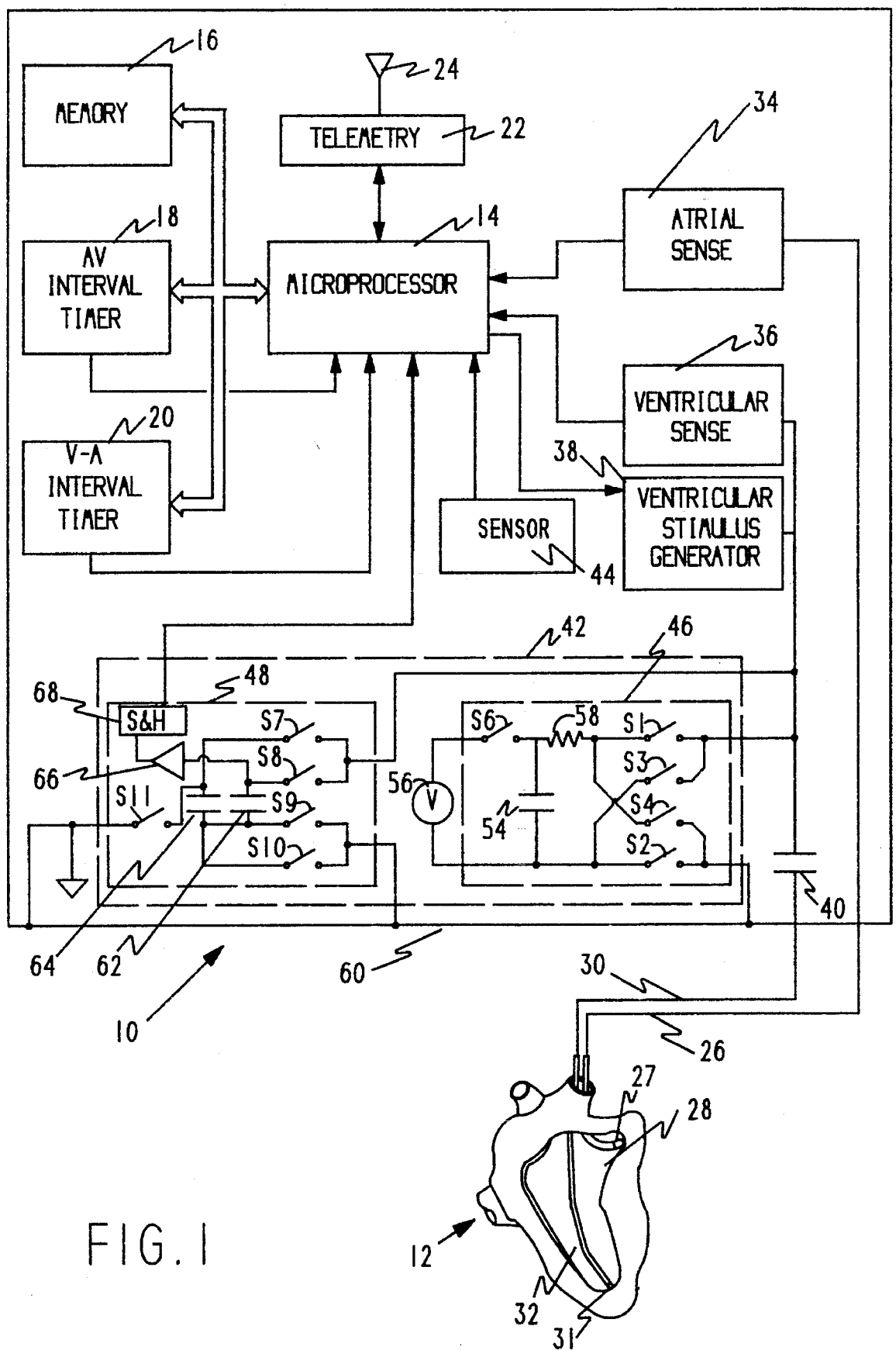
FIG. 1 is a block diagram of a first preferred embodiment of a rate adaptive pacemaker according to my invention.

Referring now to FIG. 1, a pacemaker, generally designated 10, is illustrated in schematic fashion with connection to a human heart 12. For ease of illustration, I have elected to describe my invention in connection with a pacemaker having atrial sensing and ventricular sensing and pacing. It should be understood, however, that my invention can be employed for sensing in the atrium, the ventricle or both and that both atrial or ventricular pacing or either of them could be provided without departing from the teachings of my invention. In addition, the features of my invention could also be combined with an implantable defibrillator/cardioverter.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 so that communication can be had across an antenna 24 to an external programmer (not shown). Telemetry permits an attending physician to obtain data and information from the pacemaker and to control the pacemaker to set various selectable parameters, as known in the art.

The pacemaker 10 is connected to the heart 12 through a first lead 26 to an electrode 27 in the atrium 28 and through a second lead 30 to an electrode 31 in the ventricle 32. An indifferent electrode (e.g., the pacemaker can) is provided to complete the electrical circuit through the body. In the illustrated embodiment, a can 60 or outer casing of the pacemaker serves as the indifferent electrode. Bipolar leads can also be used with my invention as well as the unipolar leads illustrated here. Atrial sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide atrial pacing, should that be desired, or to provide cardioversion/defibrillation capabilities in response to the detected condition of the heart. Stimulation of the heart is passed through a coupling capacitor 40 in a conventional fashion.

To control the pulse rate of the ventricular stimulus generator 38, the microprocessor acquires information on the condition of the heart through an impedance circuit 42. The impedance circuit 42 detects changes in impedance primarily to the changing shape of the heart, which is related to the physical shape of the heart as it beats and pumps blood. This information can be used to derive a measure of the stroke volume or ejection fraction or end diastolic volume of the heart. Furthermore, the shape of the impedance wave form can provide information on other cardiac timing parameters such as isovolumetric contraction time, pre-ejection period, and so on.

In addition to the measurement of impedance, a sensor 44 may also be provided to obtain an indication of physiologic need and adjust the pacing rate. Such a sensor may be an accelerometer, as described by Dahl, U.S. Pat. No. 4,140,132, (incorporated herein by reference) a temperature sensor, as described by Alt, U.S. Pat. No. 4,688,573 (also incorporated herein by reference), or any other suitable sensor of a parameter which may be correlated to physiologic need of the patient.

Figure 2:
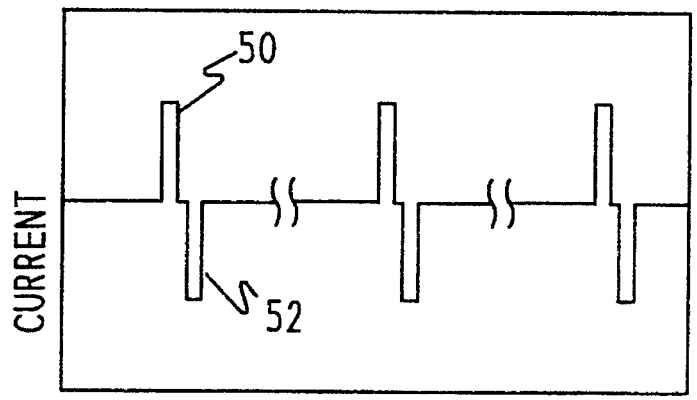
FIG. 2 is a graph of a series of biphasic pulses.

The impedance circuit 42 comprises a biphasic signal injector 46 and a signal detector 48. The biphasic signal injector 46 produces short, essentially symmetrical biphasic constant current pulses to detect the varying impedance of the heart. Each pulse has a duration on the order of one (1) to fifty (50) microseconds and an amplitude of 0.1–2 mA. The resulting detected voltage across the heart valve will be on the order of 50–1000 mV. As shown in FIG. 2, the two pulses forming a pulse pair are substantially similar in duration and amplitude, polarity being reversed. Preferably, differences in magnitude and duration between a first pulse 50 and a second pulse 52 are no more than plus or minus ten percent. Most preferably, pulse amplitude is very similar, on the order of less than 0.1% variation. Greater variability in duration is acceptable. The symmetrical nature of the pulses permits the impedance effect associated with each pulse to be additively combined as will be explained hereafter, thus doubling the apparent magnitude of impedance change, while eliminating other effects.

The signal injector 46 has a storage capacitor 54 which is connected to a voltage source 56 through a switch S6. The voltage source 56 is preferably a battery or other power source conventionally used to provide electrical power within an implantable pacemaker. The switch S6, and all of the other switches described herein, are preferably controlled by the microprocessor 14. S6 is closed to connect the capacitor 54 to the voltage source 56, charging the capacitor. A large resistor 58 is connected between the capacitor 54 and the switches. The resistor 58 is large enough to be the dominant impedance in the circuit, effectively creating a constant current source. Consequently, since the voltage on capacitor 54 would be known, and the effective impedance would be well approximated by the impedance of the resistor 58, the current flowing through the switches S1, S2, S3, S4 into and through the heart would be known. By measuring the voltage drop across the heart, as more particularly described hereafter, the impedance can therefore be easily computed. When a biphasic pulse pair is produced, the switch S6 is opened and four switches S1, S2, S3, and S4, are closed and opened under the control of the microprocessor 14.

To produce the first pulse 50, switches S1 and S2 are closed while S3 and S4 remain open. This connects a first side of the capacitor 54 and resistor 58 through switch S1 to the lead 30 and electrode 31, and simultaneously connects the second side of the capacitor 54 through switch S2 to the indifferent electrode 60. The capacitor 54 and resistor 58 are relatively large so that over the duration of the pulse 50 so that the capacitor 54 and resistor 58 are essentially a constant current source. After a selected duration, for example five microseconds, switches S1 and S2 are opened by the microprocessor 14 and switches S3 and S4 are closed. This connects a first side of capacitor 54 and the resistor 58 through switch S4 to the indifferent electrode 60 and the second side of the capacitor 54 through switch S3 to the lead 30 and electrode 31, reversing the polarity of the current pulse being applied.

Preferably each pulse lasts between one and fifty microseconds and has a current magnitude on the order of between 0.1 and 2 mA, preferably 0.5 mA. Pulse pairs are produced on the order of one hundred times per second but may be produced from two times per second to several hundred times per second. Their duration, therefore, is about one thousand times shorter than the charging period during which switch S6 is connected to the capacitor 54. Consequently, because of the relatively large size of the capacitor 54 and its comparatively long charging period compared to the amplitude and duration of the pulses, the electrical condition of the capacitor 54 is essentially constant.

Use of a balanced biphasic current pulse has the advantage that no net charge is transferred across the electrodes. This reduces electrode deposition and corrosion for greater biocompatability.

The constant current source represented by the combination of the battery 56, the switch S6, the capacitor 54 and the resistor 58, could be implemented in other forms without departing from the teachings of my invention. For example, a solid state implementation could easily be employed by those skilled in the art such as a Wilson current mirror transistor circuit. See, for example, *The Art of Electronics*, 2nd ed. Paul Horowitz and Winfield Hill Cambridge Univ. Press 1989 pgs 88–90.

Figure 6:
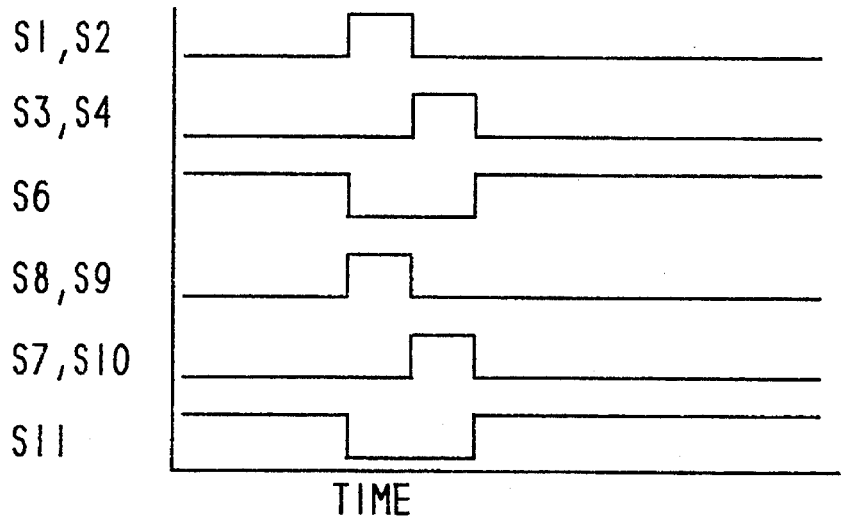
FIG. 6 is a timing diagram.

The voltages associated with the pulses of the biphasic pulse pair are detected through the detector 48. The detector 48 has two capacitors 62, 64 which are connected through four switches S7, S8, S9 and S10 to the electrode 31 and the indifferent electrode 60. During the first pulse 50, when switches S1 and S2 of the injector 46 are closed, switch S8 and S9 of the detector 48 are closed, as illustrated in timing diagram FIG. 6. This connects a first side of the first capacitor 62 through switch S8 to the lead 30 and electrode 31. A second side of the first capacitor 62 is connected through switch S9 to the indifferent electrode 60. When the first pulse 50 is over, and switches S1 and S2 are opened, switches S8 and S9 are also opened, as also shown in FIG. 6. The duration of the sampling occupies most or all of the injected current pulses, but preferably the duration $T_D$ and the size $C_s$ of the sampling capacitors 62, 64 are chosen so that $4\times(Z_{LEAD}\times C_s)=T_D$. Thus, three to four time constants are available for sampling. As a result, the sampling capacitor voltages are less sensitive to capacitive loading or timing uncertainties. During the second pulse 52, when switches S3 and S4 are closed, switches S7 and S10 are also closed, connecting the second capacitor 64 to the electrodes. Switch S7 connects a first side of the second capacitor 64 to the lead 30 and electrode 31. Switch S 10 connects a second side of the second capacitor 64 to the indifferent electrode 60. When the second pulse 52 ends and switches S3 and S4 are opened, switches S8 and S9 are also opened and a switch S11 is closed, connecting the first side of the second capacitor 64 to system ground. The second sides of both the first and second capacitor are connected together. This effectively "subtracts" the two charges from each other. Background effects, such as the intrinsic electrical condition of the heart, being common to both first capacitor 62 and second capacitor 64, would be eliminated by this subtractive combination. The desired voltage to be measured, resulting from the changing impedance of the heart, would be of opposite polarity because of the application of the biphasic current pulse. Consequently, the voltage across the series combination of the first capacitor 62 and the second capacitor 64 would be twice the voltage drop associated with a particular level of current injected through the heart. To make the desired measurement, the first side of the first capacitor 62 is connected to a buffer 66 which presents a high impedance. The output of the buffer 66 communicates with a sample-and-hold circuit 68 which samples the combined voltages of the first and second capacitor 62, 64. Alternatively, the first and second capacitor 62, 64 themselves can act as a sample and hold circuit. The value of this voltage is communicated from the sample-and-hold circuit 68 to the microprocessor 14 which uses the information to calculate the impedance of the heart 12.

Figure 3:
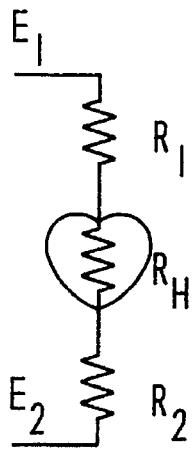
FIG. 3 is a schematic representation of a configuration of electrodes for measuring cardiac impedance.
Figure 4:
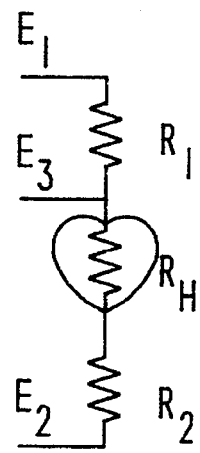
FIG. 4 is a schematic representation of a second configuration of electrodes for measuring cardiac impedance.
Figure 5:
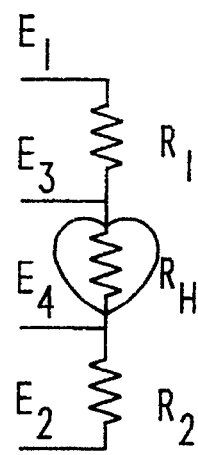
FIG. 5 is a schematic representation of a third configuration of electrodes for measuring cardiac impedance.

In FIG. 1, I have illustrated the biphasic signal injector 46 and the signal detector 48 using the same electrodes 31,60. This configuration is illustrated diagrammatically in FIG.3. FIG. 3 illustrates a first electrode E1 connected to a second electrode E2 through three lumped impedances or resistances R1, RH and R2. The resistances R1 and R2 may be associated with effects such as resistance in the leads themselves, resistance in other parts of the body or other signals or the effect of the interface between the electrode and the body. The impedance or resistance RH, representing the impedance of the heart, is the primary parameter which I desire to measure accurately but other impedances, such as ventilation could also be selected. Although the desired changing impedance RH may be effectively measured using the configuration of FIG. 3, it is also possible to attempt to eliminate the effects of the other resistances R1 and R2 by utilizing additional electrodes. In the apparatus of my invention, this is possible because the injector 46 and detector 48 are separate and distinct. For example, switches S7 and S8 of the detector 48 could be connected, not to the ventricular lead 30 and ventricular electrode 31, but to the atrial lead 26 and atrial electrode 27. This situation is represented diagrammatically in FIG. 4. In FIG. 4, three electrodes E1, E2 and E3 are illustrated. The detector 48 and injector 46 share a common electrode, for example electrode E2. This would represent a three electrode configuration. In addition, the injector 46 and the detector 48 may share no common electrodes. For example, the injector 46 could be connected through a bipolar electrode into the ventricle and the detector could be connected through a bipolar lead into the atrium. This configuration is illustrated diagrammatically in FIG. 5. The injector 46 might utilize electrodes E1 and E2, while the detector 48 would utilize electrode E3 and a fourth electrode E4. Additional electrode configurations could easily be selected to obtain the most favorable response or measurement of the changing impedance of the heart. Any of the electrodes E1, E2, E3 or E4 could be subdivided to connect to multiple locations within the patient's body.

Having identified impedance information associated with cardiac contractions, this information can then be used to control the pacing rate or other pacing parameters, such as A-V delay intervals. By controlling the pacing rate in such a manner as to keep the stroke volume, pre-ejection interval, or ejection fraction relatively constant from cycle to cycle, a physiologically appropriate pacing rate is selected.

My invention may be embodied in other specific forms without departing from the spirit or essential characteristics thereof. The foregoing description is, therefore, to be viewed in all respects as illustrative and not restrictive. The scope of my invention is defined by the appended claims.

I claim as my invention:

1. A cardiac stimulation apparatus comprising
   means for stimulating a patient's heart;
   means for measuring impedance within the patient's body, said impedance measuring means including
      means for producing a constant current biphasic pulse pair, said pulse pair having a first pulse having current flowing in a first direction and a second pulse having current flowing in a second direction, means for electrically transmitting said pulse pair through at least a portion of said patient's body,
      means for detecting a first voltage associated with said first pulse across at least a part of said patient's body,
      means for producing a first signal proportional to said first voltage,
      means for detecting a second voltage associated with said second pulse across at least a part of said patient's body,
      means for producing a second signal proportional to said second voltage, and
      means for producing a combined signal from said first and second signals,
   means for deriving a metabolic demand parameter from said combined signal; and
   means for adjusting said means for stimulating said patient's heart in relation to said metabolic demand parameter.

2. The cardiac stimulation apparatus according to claim 1 wherein said means for producing a constant current biphasic pair comprise means for producing a plurality of biphasic pairs.

3. The cardiac stimulation apparatus according to claim 1 wherein said means for producing a combined signal comprise means for subtracting said second signal from said first signal.

4. The cardiac stimulation apparatus according to claim 3 wherein said means for subtracting said second signal from said first signal comprise a first capacitor for storing said first voltage, a second capacitor for storing said second voltage, and means for connecting said first and second capacitors in series.

5. The cardiac stimulation apparatus according to claim 4 wherein said means for electrically transmitting said pulse pair comprise a first electrode and a second electrode and wherein said means for producing said biphasic constant current pulse pair comprise
   a constant current source having a first electrical pole and a second electrical pole,
   a first switch for connecting said first electric pole to said first electrode during a first selected period of time, a second switch for connecting said second electric pole to said second electrode during said first selected period of time, a third switch for connecting said first electric pole to said second electrode during a second selected period of time, and a fourth switch for connecting said second electric pole to said first electrode during said second selected period of time.

6. The cardiac stimulation apparatus according to claim 5 wherein said constant current source comprises a source of electrical power, a capacitor electrically connected to said source of power, and a resistor electrically connected in series to said capacitor and to said first switch and said third switch.

7. The cardiac stimulation apparatus according to claim 1 wherein said means for electrically transmitting said pulse pair comprise a first electrode and a second electrode and wherein said means for producing said biphasic constant current pulse pair comprise a constant current source having a first electrical pole and a second electrical pole, a first switch for connecting said first electric pole to said first electrode during a first selected period of time, a second switch for connecting said second electric pole to said second electrode during said first selected period of time, a third switch for connecting said first electric pole to said second electrode during a second selected period of time, and a fourth switch for connecting said second electric pole to said first electrode during said second selected period of time.

8. The cardiac stimulation apparatus according to claim 7 wherein said constant current source comprises a source of electrical power, a capacitor electrically connected to said source of power, and a resistor electrically connected in series to said capacitor and to said first switch and said third switch.

9. The cardiac stimulation apparatus according to claim 8 wherein said first pulse has a first current amplitude and said second pulse has a second current amplitude and said first and second amplitudes are substantially equivalent.

10. The cardiac stimulation apparatus according to claim 9 wherein said first pulse is between 1 microseconds and 50 microseconds in duration and said second pulse is between 1 microseconds and 50 microseconds in duration.

11. The cardiac stimulation apparatus according to claim 10 wherein the duration of said second pulse is substantially equivalent to the duration of said first pulse.

12. The cardiac stimulation apparatus according to claim 1 wherein said first pulse is between 1 microseconds and 50 microseconds in duration and said second pulse is between 1 microseconds and 50 microseconds in duration.

13. The cardiac stimulation apparatus according to claim 12 wherein the duration of said second pulse is substantially equivalent to the duration of said first pulse.

14. The cardiac stimulation apparatus according to claim 13 wherein said first pulse has a first current amplitude and said second pulse has a second current amplitude and said first and second amplitudes are substantially equivalent.

15. The cardiac stimulation apparatus according to claim 14 wherein said second amplitude differs from said first amplitude by less than about 0.1%.

16. The cardiac stimulation apparatus according to claim 15 wherein the duration of said second pulse differs from said first pulse by less than about 10%.

17. The cardiac stimulation apparatus according to claim 1 wherein said first pulse has a first current amplitude and said second pulse has a second current amplitude and said first and second amplitudes are substantially equivalent.

18. The cardiac stimulation apparatus according to claim 17 wherein said second amplitude differs from said first amplitude by less than about 10%.

19. The cardiac stimulation apparatus according to claim 18 wherein said second amplitude differs from said first amplitude by less than about 0.1%.

20. A method of detecting a changing impedance within a patient's body comprising the steps of producing a constant current biphasic pulse pair, said pulse pair having a first pulse having current flowing in a first direction and a second pulse having current flowing in a second direction, transmitting said pulse pair through at least a portion of said patient's body, detecting a first voltage associated with said first pulse across at least a part of said patient's body, producing a first signal proportional to said first voltage, detecting a second voltage associated with said second pulse across at least a part of said patient's body, producing a second signal proportional to said second voltage, producing a combined signal from said first and second signals, and deriving an impedance from said combined signal.

* * * * *